US005800558A

United States Patent [19]
LaHaise, Sr.

[11] Patent Number: 5,800,558
[45] Date of Patent: Sep. 1, 1998

[54] HIP PROSTHESIS

[76] Inventor: Gerard A. LaHaise, Sr., 275 Anthony Mill Rd., Bechtelsville, Pa. 19505

[21] Appl. No.: 802,256

[22] Filed: Feb. 19, 1997

[51] Int. Cl.$^6$ .................................. A61F 2/36; A61F 2/34
[52] U.S. Cl. .................................... 623/23; 623/22
[58] Field of Search .................... 623/22, 23, 19; 606/65–67

[56] References Cited

U.S. PATENT DOCUMENTS

| | | |
|---|---|---|
| 3,740,769 | 6/1973 | Haboush . |
| 4,822,369 | 4/1989 | Oueveau et al. . |
| 4,842,605 | 6/1989 | Sonnerat et al. . |
| 5,037,438 | 8/1991 | Davidson . |
| 5,201,771 | 4/1993 | Belykh et al. . |
| 5,376,126 | 12/1994 | Lin ............................. 623/23 |
| 5,383,938 | 1/1995 | Rohr et al. . |
| 5,389,107 | 2/1995 | Nassar et al. . |
| 5,425,778 | 6/1995 | Zichner et al. . |
| 5,556,434 | 9/1996 | Epstein et al. ................. 623/22 |

FOREIGN PATENT DOCUMENTS

89/11837  12/1989  WIPO ........................... 623/23

Primary Examiner—David H. Willse
Attorney, Agent, or Firm—Richard C. Litman

[57] ABSTRACT

A total hip joint replacement prosthesis achieves mechanical integrity and dynamic stability without requiring an axial cavity to be bored into the femur, minimizes interfacial friction to reduce the proliferation of wear generated particles and establishes secure fixation of all components to extend implant lifetime and improve implant performance. Interactive femoral and acetabular components engage a femoral shoulder and a pelvic acetabular cavity, respectively. The femoral component comprises medial and lateral clamps, which engage the femoral shoulder. The acetabular component is secured within pelvic acetabular cavity, having a ball that incorporates two sets of oppositely disposed roller bearings. A substantially cylindrical channel extends between the sets of roller bearings to receive a bearing shaft, which cooperates with the roller bearings to facilitate rotational movement between the acetabular component and the femoral component. A bolt secures a cuboidal member of the acetabular component within a cuboidal cavity of the femoral component, comprising the connection between the femoral and acetabular components of the hip prosthesis device. A protective retainer stabilizes the acetabular component. The modular nature of the components of the device allows a less traumatic surgical operation than devices incorporating a femoral stem component.

9 Claims, 3 Drawing Sheets

HIP PROSTHESIS

BACKGROUND OF THE INVENTION

1. Field of the Invention

The present invention relates to implants for total hip joint replacement, and more specifically, to hip prosthesis devices requiring minimal bone penetration for fixation thereto.

2. Description of the Prior Art

The widespread incidence of joint replacement surgery, known as arthroplasty, has prompted a surge in implant technology. For example, in people of all ages, arthritis and fall-related hip fractures warrant total hip joint prosthesis implants. The design of total hip joint prostheses calls for an interdisciplinary approach considering many factors, including mechanical integrity, dynamic stability, material durability, compatibility with a patient's body and cooperation at the interface of articulating implant components.

Total hip joints comprise interactive femoral and acetabular components, to emulate the ball-socket mechanism of a natural hip joint. Well-known means for fixing the femoral component involve the boring of an axial cavity in the femur for receiving the shaft of a femoral component. Examples of this class of total hip replacement include the prostheses described in U.S. Pat. Nos. 3,740,769, 5,037,438, 5,201,771 and 5,389,107. The introduction of the femoral stems of these implants into an axial cavity in the femur requires the resection of the top of the femur, and creates a traumatic condition within the body of the patient, requiring several months of recovery thereafter. Furthermore, the invasive fixation technique for the femoral stem creates a potentially hazardous situation, increasing the occurrence of infection, bone and soft tissue morbidity, implant loosening, pain and inflammation at the implant site and wear-particle accumulation. These conditions in turn warrant a revision surgery, which is complicated by the need to remove the original implant and further resect the already traumatized femur for the placement of a second implant.

The acetabular component of well-known total hip replacement devices comprises an acetabular cup, fixed within the pelvis for receiving the ball of the femoral component. Articulation of the implant components at the ball-cup interface creates friction, which generates wear particles that accumulate and pose a serious health threat, both locally and elsewhere within the body, to a total hip joint replacement prosthesis recipient. Mechanical instability at the ball-cup interface also accounts for failure of total hip joint replacement prostheses.

U.S. Pat. Nos. 4,822,369 and 5,389,107 disclose total hip joint replacement devices incorporating shock absorbent materials in the acetabular cup component, with which to stabilize the operation of the joint. The ball component of the total hip joint replacement device of U.S. Pat. No. 4,842,605 incorporates a double bearing to eliminate friction at the ball-cup interface, ultimately aiming to reduce the generation of wear particles and the adverse effects associated therewith. Unfortunately, the femoral component of the total hip joint replacement devices of '369, '107 and '605 also require insertion thereof into the potentially problematic axial femoral cavity.

Fixation of the acetabular cup within the pelvis presents another problematic aspect of total hip joint replacement systems. Well known means for securing the acetabular cup component to the bone surface of the pelvis include bone cement and screws. Loosening of the acetabular cup can cause pain, irritation, the generation of additional wear particles and ultimately, the mechanical failure of the hip prosthesis system. U.S. Pat. Nos. 5,383,938 and 5,425,778 disclose means for internally securing the acetabular cup component within the pelvic socket, namely a locking ring and a supporting ring, respectively.

In light of the shortcomings of the above inventions and patents, there is a need for an improved total hip joint replacement prosthesis that achieves mechanical integrity and dynamic stability without requiring an axial cavity to be bored in the femur. There is also a need for a total hip joint replacement prosthesis that minimizes interfacial friction to reduce the proliferation of wear-generated particles and establishes secure fixation of all components to extend implant lifetime and improve implant performance.

None of the above inventions and patents, taken either singly or in combination, is seen to describe the instant invention as claimed.

SUMMARY OF THE INVENTION

The total hip joint replacement prosthesis of the present invention achieves mechanical integrity and dynamic stability without requiring an axial cavity to be bored in the femur. At the same time, the total hip joint replacement prosthesis of the present invention minimizes interfacial friction to reduce the proliferation of wear-generated particles and establishes secure fixation of all components to extend implant lifetime and improve implant performance.

The present invention comprises interactive femoral and acetabular components, that engage a femoral shoulder and a pelvic acetabular cavity, respectively. The femoral component comprises medial and lateral clamps, which engage the femoral shoulder. The medial clamp incorporates upper and lower substantially semi-circular members that integrally connect to a bridge member in a substantially frusto-conical formation. The upper and lower semi-circular members are opposingly disposed to sandwich the femoral shoulder therebetween. Screw-aperture connective means secure the medial clamp to the lateral clamp, a substantially hemispherical one-piece member, to ultimately enclose the femoral shoulder without invasive surgical penetration thereof. The femoral component is fabricated from well-known biocompatible materials having the mechanical and structural properties necessary for load-bearing joint replacement applications.

The acetabular component of the present invention, formed of shock-absorbent material, is secured within pelvic acetabular cavity in a well-known fashion, and receives a ball. The ball incorporates a bearings housing, being substantially cylindrical, with two sets of opposingly disposed roller bearings within. A substantially cylindrical channel extends between the sets of roller bearings.

A hub assembly operatively connects the ball, and its interior components to the bridge member of the femoral component of the device. The hub assembly comprises a disc having a substantially cylindrical bearing shaft extending therefrom, which insertably engages the cylindrical channel, retained therein by the roller bearings. A hemispherical hub extends from the other side of the disc and forms a continuous spherical surface with the ball when the hub assembly is in place.

A substantially cuboidal member extends from the hemispherical hub in a substantially axial direction of the femoral shoulder, and insertably engages a cuboidal cavity in the bridge member. A bolt secures the cuboidal member in the cuboidal cavity, comprising the connection between the femoral and acetabular components of the hip prosthesis device.

A protective retainer stabilizes the components of the bearings-ball-hub assembly within the pelvic cavity. The retainer comprises a slightly-curved annular ring and a raised, inwardly-curved annular ring, integrally attached to each other. A flat annular ring overlays the retainer, enabling connective elements to engage the pelvic cavity, securing the retainer thereto.

All elements of the acetabular component are fabricated from well-known biocompatible materials having the mechanical and structural properties necessary for load-bearing joint replacement applications.

Operation of the hip prosthesis in the ventral-dorsal (front-to-back) plane of motion involves rotational interaction of the roller bearings and the bearing shaft. The connection established by the cuboidal member and the bridge member stabilizes the femoral components of the prosthesis during ventral-dorsal motion. This system substitutes for the ball-socket ventral-dorsal articulation within the acetabular cup to minimize interfacial fraction and the generation of wear particles. Accordingly, the safety and longevity of the hip prosthesis are improved.

Articulation between the ball and the inner surface of the acetabular cup facilitates medial-lateral (side-to-side) motion. The protective retainer stabilizes the ball within the pelvic cavity. Motion in the medial-lateral plane involves substantially less weight-bearing. Accordingly, minimal wear particle generation occurs.

In the event a revision surgery is required with a recipient of the total hip joint replacement of this invention, the modular nature of the components of the device would allow a less traumatic operation than with devices incorporating the femoral stem component.

Accordingly, it is a principal object of the invention to achieve mechanical integrity and dynamic stability without requiring an axial cavity to be bored in the femur for the fixation of the implant.

It is another object of the invention to minimize interfacial friction to reduce the proliferation of wear-generated particles.

It is a further object of the invention to establish the secure fixation of all components to extend implant lifetime and improve implant performance.

Still another object of the invention is to facilitate a less traumatic operation in the event a revision surgery is required.

It is also an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
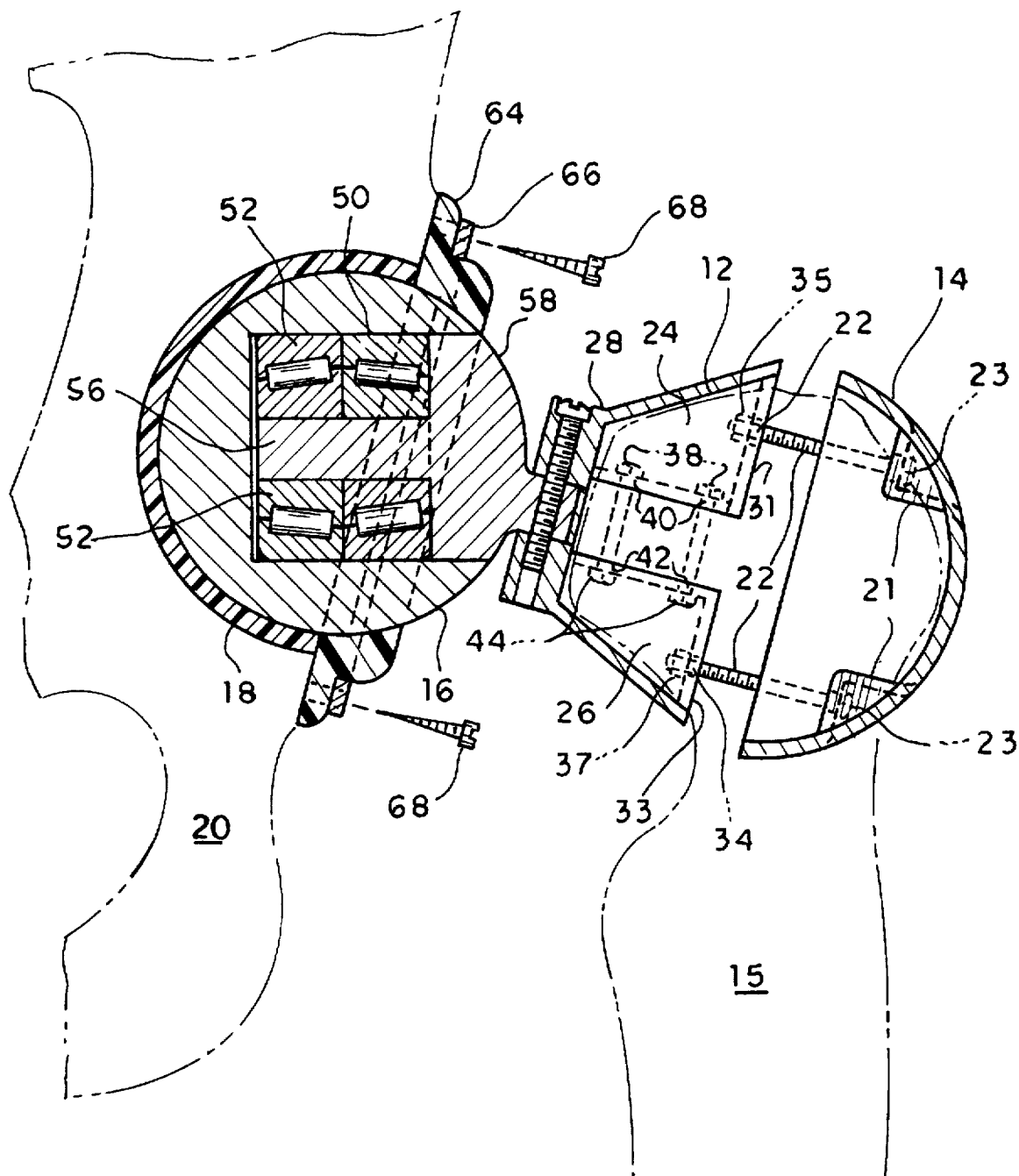
FIG. 1 is an environmental, cross-sectional view of the hip prosthesis of the present invention.
Figure 2:
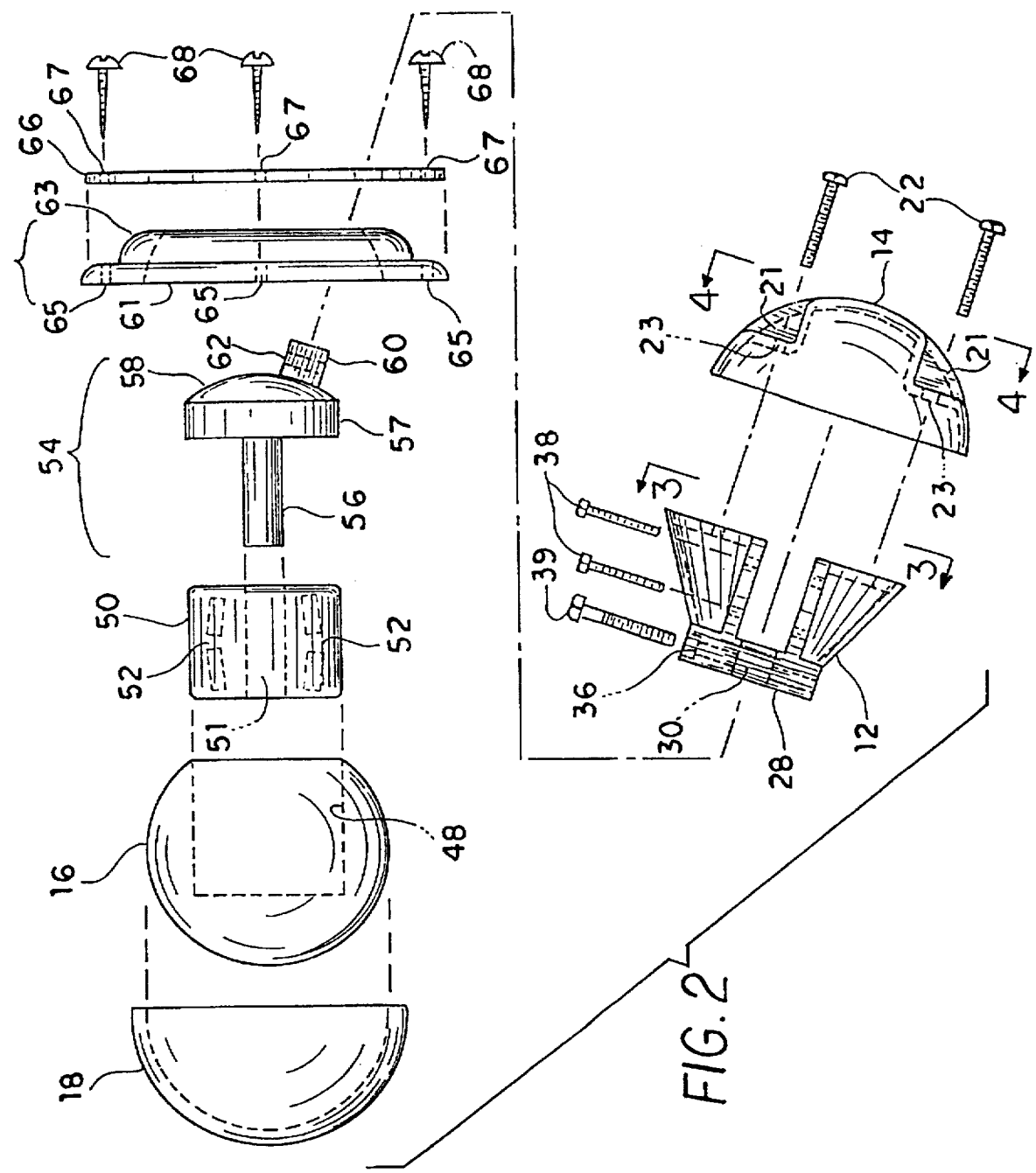
FIG. 2 is an exploded elevational view of the components of the hip prosthesis according to FIG. 1.
Figure 3:
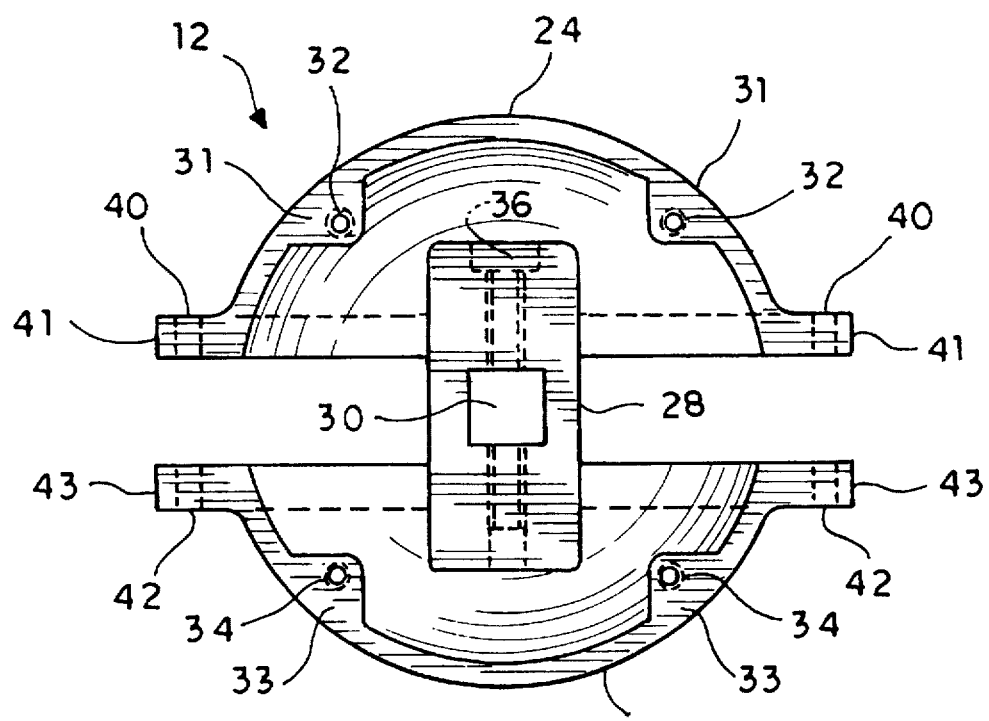
FIG. 3 is a cross-sectional view of the medial femoral component along line 3—3 in FIG. 2.

The present invention, comprises interactive femoral and acetabular components, as shown engaging a femoral shoulder 15 and a pelvic acetabular cavity 20, respectively, in FIG. 1. The femoral component of the present invention comprises medial and lateral clamps 12 and 14. Medial clamp 12 engages the medial femoral shoulder, and incorporates upper and lower substantially semi-circular members 24 and 26, respectively, as illustrated in FIG. 3. Upper and lower semi-circular members 24,26 integrally connect to a bridge member 28, medial thereto, to form a substantially frusto-conical formation. Upper and lower semi-circular members 24,26 are opposingly disposed to sandwich the medial femoral shoulder therebetween. Inward protrusions 31 extend along the inner surface of upper semi-circular member 24 on the ventral and dorsal sides thereof, and define apertures 32. Inward protrusions 33 extend along the inner surface of lower semi-circular member 26 on the ventral and dorsal sides thereof, and define apertures 34. Upper and lower semi-circular members 24,26 comprise flanges 41 and 43, respectively, which extend ventrally and dorsally from the edges thereof. Flanges 41,43 define a plurality of apertures 40,42, respectively, which align to receive bolts 38, as shown in FIG. 2. Nuts 44 retain bolts 38 to secure upper and lower semi-circular members 24,26 about the medial femoral shoulder, as shown in FIG. 1.

Bridge member 28 lies adjacent to the medial surface of the femoral shoulder, and extends medially therefrom. Bridge member 28 has a substantially rectangular cross-section and defines a bolt-receiving aperture 36. Bridge member 28 also defines a substantially cuboidal cavity 30 in its substantial center opening through bolt-receiving aperture 36.

Figure 4:
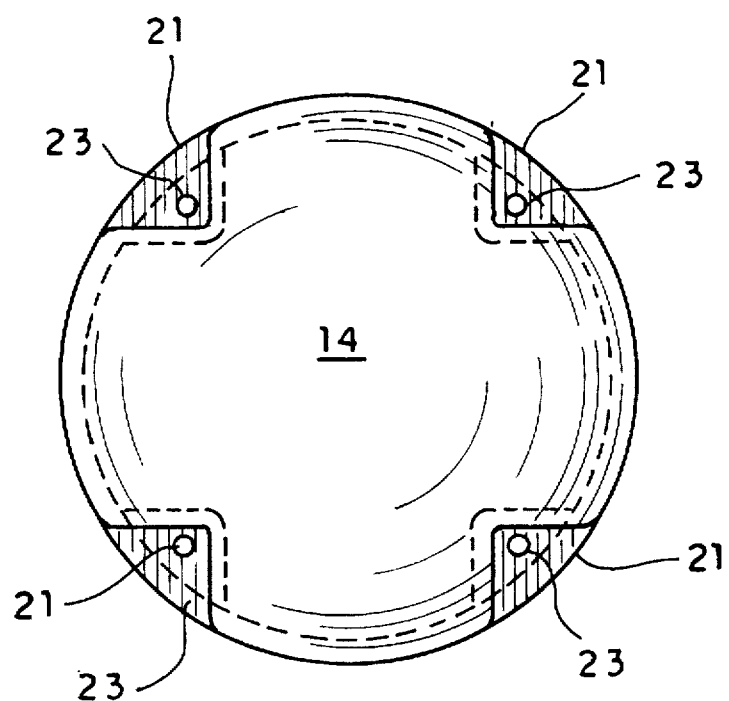
FIG. 4 is a cross-sectional view of the lateral femoral component along line 4—4 in FIG. 2.

Lateral clamp 14 of the femoral component, as shown in FIG. 4, is a substantially hemispherical one-piece member, which engages the lateral section of the femoral shoulder. Inward protrusions 21 extend along the upper and lower inner surfaces of lateral clamp 14 on the ventral and dorsal sides thereof, and define apertures 23. When medial and lateral clamps 12,14 engage the respective parts of the femoral shoulder, apertures 23 of the upper inner surface of lateral clamp 14 align with apertures 32 of upper semi-circular member 24 of medial clamp 12, to receive bolts 22. Additionally, apertures 23 of the lower inner surface of lateral clamp 14 align with apertures 34 of lower semi-circular member 26 of medial clamp 12, to receive bolts 22. Nuts 35,37 retain bolts 22 to secure upper and lower semi-circular members 24,26 to lateral clamp 14, respectively.

The femoral component connective elements of the present invention secure medial and lateral clamps 12,14 about the femoral shoulder without invasive surgical penetration of the bone, as shown in FIG. 1. The femoral component is fabricated from well-known biocompatible materials having the mechanical and structural properties necessary for load-bearing joint replacement applications.

FIG. 2 illustrates the acetabular component of the present invention. An acetabular cup 18, formed of shock-absorbent material, is secured within pelvic acetabular cavity in a well-known fashion, and receives ball 16. Ball 16 in turn defines a substantially cylindrical cavity 48, which receives a substantially cylindrical bearings housing 50. Bearings housing 50 contains two sets of opposingly disposed roller bearings 52. A substantially cylindrical channel 51 extends along the central longitudinal axis of bearings housing 50, between the sets of roller bearings 52. Bearings housing 50 and roller bearings 52 can be drop-forged, or otherwise machined, so that roller bearings 52 and bearings housing 50 are integral components, and further, can be built into ball 16.

A hub assembly 54 operatively connects ball 16, and its interior components, with bridge member 28 of medial femoral clamp 12. A disc 57 integrally engages a substantially cylindrical bearing shaft 56, extending from the substantial center of the circular surface of disc 57. Bearing shaft 56 insertably engages cylindrical channel 51, and is retained therein by roller bearings 52. A hemispherical hub 58 integrally connects to the circular surface of disc 57 that is opposite to the surface engaging bearing shaft 56. When bearing shaft 56 fully insertably engages cylindrical channel 51, hemispherical hub 58 forms a continuous spherical surface with ball 16.

A substantially cuboidal member 60 integrally connects with hemispherical hub 58, extending laterally therefrom, at an angle so as to be in the substantial axial direction of the femoral shoulder. Cuboidal member 60 insertably engages cuboidal cavity 30 of bridge member 28, and defines an aperture 62 that is continuous with bolt-receiving aperture 36, to accommodate a bolt 39. Bolt 39 thus connects the femoral and acetabular components of the hip prosthesis device.

A protective retainer 64 stabilizes the components of the bearings-ball-hub assembly within pelvic cavity 20. Retainer 64 comprises a slightly-curved annular ring 61 and a raised, inwardly-curved annular ring 63, integrally attached to annular ring 61. Annular ring 61 defines a plurality of apertures 65, and engages the outer surface of pelvic cavity 20. A flat annular ring 66 defines a plurality of apertures 67 and overlays retainer 64 so that apertures 67 align with apertures 65. Screws 68 engage apertures 67 and apertures 65, ultimately engaging pelvic cavity 20 to secure retainer 64 thereto.

All elements of the acetabular component are fabricated from well-known biocompatible materials having the mechanical and structural properties necessary for load-bearing joint replacement applications.

Roller bearings 52 facilitate the rotation of bearing shaft 56 for operating the hip prosthesis of the present invention in the plane of ventral-dorsal (front-to-back) motion. The connection established by cuboidal member 60 and bridge member 28 stabilizes the femoral components of the prosthesis during ventral-dorsal motion. The operation of the roller bearings 52 and bearing shaft 56 substantially eliminate the articulation between ball 16 and the inner surface of acetabular cup 18 during ventral-dorsal motion, minimizing interfacial friction and the generation of wear particles. Accordingly, the safety and longevity of the hip prosthesis are improved.

Articulation between ball 16 and the inner surface of acetabular cup 18 facilitates medial-lateral (side-to-side) motion. Protective retainer 64 stabilizes the rotation of ball 16 within pelvic cavity 20. Motion in the medial-lateral plane involves substantially less weight-bearing. Accordingly, minimal wear particle generation occurs.

The clamping mechanism of femoral component 14 allows secure fixation without inducing trauma to the femur. The screw-aperture assemblies are external to the femur, and avoid the problems associated with implants requiring internal bone fixation.

In the event a revision surgery is required with a recipient of the total hip joint replacement of this invention, the modular nature of the components of the device would allow a less traumatic operation than with devices incorporating the femoral stem component.

It is to be understood that the present invention is not limited to the sole embodiment described above, but encompasses any and all embodiments within the scope of the following claims.

I claim:

1. A total hip joint replacement prosthesis comprising:
   a femoral component including
      a medial clamp comprising upper and lower substantially semi-circular members, a bridge member and means for securing said upper and lower semi-circular members together, said upper and said lower semi-circular members opposingly disposed to sandwich a femoral shoulder therebetween and integrally attached to said bridge member in a substantially frusto-conical formation, said bridge member having a substantially rectangular cross section;
      a lateral clamp comprising a substantially hemispherical member, said hemispherical member dimensioned and configured to engage a femoral shoulder; and,
      means for connecting said lateral clamp to said medial clamp about a femoral shoulder to allow secure external fixation thereto; and,
   an acetabular component including
      an acetabular cup for placement within a pelvic acetabular cavity;
      a ball dimensioned and configured to be closely received by said acetabular cup to allow universal rotation when placed within said acetabular cup, including a roller bearings assembly;
      a hub assembly comprising means for cooperating with said roller bearings assembly to facilitate rotational movement between said acetabular component and said femoral component, and means for insertably connecting said ball to said bridge member of said femoral component;
      a protective retainer, said retainer comprising a slightly-curved annular ring and a raised, inwardly-curved annular ring, said slightly-curved annular ring defining a plurality of apertures; and,
      means for securing said protective retainer to the outer surface of a pelvic bone.

2. The total hip joint replacement prosthesis according to claim 1, said upper and lower substantially semi-circular members each having a plurality of flanges, each of said flanges defining an aperture, each said aperture of said upper substantially semi-circular member being in registry with an associated aperture of said lower substantially semi-circular member, and wherein said means for securing said upper and lower semi-circular members together comprises a bolt-nut assembly that operably secures said upper and lower semi-circular members by a bolt passing through a pair of apertures in registry.

3. The total hip joint replacement prosthesis according to claim 1, said lateral clamp and said medial clamp further comprising a plurality of inward protrusions along the length thereof, said inward protrusions defining a plurality of alignable apertures, wherein said means for connecting said lateral clamp to said medial clamp about a femoral shoulder comprises a bolt-nut assembly that operably engages said alignable apertures.

4. The total hip joint replacement prosthesis according to claim 1, said bridge member dimensioned and configured to lie adjacent to the medial surface of a femoral shoulder, and defining a bolt-receiving aperture and a substantially cuboidal cavity in substantially the center of said bridge member.

5. The total hip joint replacement prosthesis according to claim 4, said roller bearings assembly comprising a bearings housing and upper and lower sets of opposingly disposed roller bearings, said bearings housing enclosing said sets of opposingly disposed roller bearings in turn defining a substantially cylindrical channel between said sets of opposingly disposed roller bearings.

6. The total hip joint replacement prosthesis according to claim 5, said hub assembly comprising a disc comprising two opposing circular surfaces and a hemispherical hub integrally connected to one of said circular surfaces of said disc, said hemispherical hub positioned relative to said ball to form a continuous spherical surface with said ball.

7. The total hip joint replacement prosthesis according to claim 6, said means for cooperating with said roller bearings assembly to facilitate rotational movement between said acetabular component and said femoral component comprising a substantially cylindrical bearing shaft, said bearing shaft integrally connected to and extending from the substantial center of said circular surface of said disc opposite to said circular surface connected to said hemispherical hub, whereby said bearing shaft insertably engages said cylindrical channel, and is retained therein by said upper and lower sets of opposingly disposed roller bearings.

8. The total hip joint replacement prosthesis according to claim 6, said means for insertably connecting said ball to said bridge member of said femoral component comprising a substantially cuboidal member, said cuboidal member integrally connected to said hemispherical hub, extending laterally therefrom at a predetermined angle said cuboidal member to insertably engage said cuboidal cavity of said bridge member, and defining an aperture that is continuous with said bolt-receiving aperture to accommodate a bolt therein.

9. The total hip joint replacement prosthesis according to claim 1, said means for securing said protective retainer to the outer surface of a pelvic bone comprising a flat annular ring and cooperating screws, said flat annular ring defining a plurality of apertures and overlaying said protective retainer so that said flat annular ring apertures align with said protective retainer apertures and said screws engage said flat annular ring apertures and said protective retainer apertures.

* * * * *